United States Patent
Axelsson et al.

(10) Patent No.: US 6,479,491 B1
(45) Date of Patent: Nov. 12, 2002

(54) DISUBSTITUTED MORPHOLINE, OXAZEPINE OR THIAZEPINE DERIVATIVES, THEIR PREPARATION AND THEIR USE AS DOPAMINE D4 RECEPTOR ANTAGONISTS

(75) Inventors: Oskar Axelsson, Malmo; Dan Peters, Arlov, both of (SE); Jorgen Scheel-Kruger, Glostrup; Elsebet Ostergaard Nielsen, Copenhagen, both of (DK)

(73) Assignee: Neurosearch A/S, Glostrup (DK)

( * ) Notice: Subject to any disclaimer, the term of this patent is extended or adjusted under 35 U.S.C. 154(b) by 0 days.

(21) Appl. No.: 09/709,297

(22) Filed: Nov. 13, 2000

Related U.S. Application Data

(62) Division of application No. 09/242,693, filed as application No. PCT/EP97/04587 on Aug. 22, 1997.

(30) Foreign Application Priority Data

Aug. 23, 1996 (DK) ................................. 0883/96

(51) Int. Cl.⁷ .................... A61K 31/535; C07D 265/30; A61P 25/00
(52) U.S. Cl. ................. 514/237.5; 514/237.8; 514/238.2; 514/238.8; 514/239.2; 544/158; 544/159; 544/162; 544/163; 544/164; 544/165; 544/166; 544/167; 544/168; 544/169; 544/170; 544/171; 544/172; 544/173; 544/174
(58) Field of Search ............ 514/237.5, 537.8, 514/238.2, 238.5, 238.8; 544/158, 159, 162, 163, 164, 165, 166, 167, 168, 169, 170, 171, 172, 173, 174

(56) References Cited

FOREIGN PATENT DOCUMENTS

| DE | 2340874 A | 2/1974 |
|---|---|---|
| DE | 2436398 A | 2/1975 |
| DE | 2446046 A | 4/1975 |
| DE | 2459089 | 6/1975 |
| DE | 2519101 A | 11/1975 |
| EP | 0000693 A | 2/1979 |
| GB | 1260886 A | 1/1972 |
| GB | 1310236 A | 3/1973 |
| JP | 49-82677 | 8/1974 |
| JP | 01-117860 | 5/1989 |
| JP | 02-104572 | 4/1990 |
| WO | 93 15052 | 8/1993 |
| WO | 95 14690 | 6/1995 |
| WO | 95 33723 | 12/1995 |

OTHER PUBLICATIONS

G.P. Reynoldsm *Drugs*, vol. 51(1), pp. 7–11 (1996).
Nakanishi et al., *Chemical Abstracts*, 164204g, vol. 83 (1975).
Izquierdo et al., *Chemical Abstracts*, 90:186971 (1979).
Ici, *Chemical Abstracts*, 88:62400 (1978).
Harada et al., *Chemical Abstracts*, 124:55916 (1995).
Hery et al., *Chemical Abstracts*, 94:139617 (1994).
M.S. Hadley, Medicinal Research Reviews, vol. 16, No. 6, Jun. 1996, pp. 507–526.
J. Ohmori et al, Journal of Medicinal Chemistry, vol. 39, No. 14, 5, Jul. 1996, pp. 2763–2772.
Chemical Abstract: vol. 112, No. 1 Jan. 1, 1990, T. Kon et al.
Chemical Abstract: vol. 113, No. 15, Oct. 8, 1990, T. Kon et al.
T. Moore et al, Chemical & Pharmaceutical Bulletin, vol. 43, No. 7, Jul. 1995, pp. 1137–1147.
H. Harada et al, Chemical & Pharmaceutical Bulletin, vol. 43, No. 8m Aug. 1995, pp. 1364–1378.
Abstract, Muro et al., Yakugaku Zasshi (1986), 106(9), 964–74.
Abstract, Pifieri et al., Eur. J. Med. Chem –Chim. Ther. (1983), 18(5), 465–7.
Abstract, Fukuzawa et al., JP 51128984 761110 Showa.
Abstract, Fukuzawa et al., JP 51128984 761116 Showa.
Abstract, Nakanishi et al., JP 49082675 740808 Showa.
Abstract, WO 9807710 980226.

*Primary Examiner*—Brenda Coleman
(74) *Attorney, Agent, or Firm*—Birch, Stewart, Kolasch & Birch, LLP

(57) ABSTRACT

The present invention relates to compounds of formula (I), any of it enantiomers, or any mixture thereof, or a pharmaceutically acceptable acid addition salt thereof, wherein $R^1$, $R^2$, $R^3$, $R^4$, $R^{11}$, $R^{12}$, $R^{13}$, $R^{14}$ and $R^{15}$ each independently are hydrogen, alkyl, alkoxy, halogen, trifluoromethyl, nitro, cyano, amino, acyl, alkylamino, dialkylamino, aminocarbonyl, or acylamino; R5 is hydrogen, alkyl, alkoxyalkyl, or phenylalkyl; X is —$CH_2$—Z—, Z—$CH_2$—, NH—CO—, —CO—NH—, or —CH=CH—; wherein Z is O, S, $CH_2$, or NH; Y is O, —$CH_2$—W—, —W—$CH_2$—; wherein W is O, or S; and n is 0, 1 or 2. The compounds are useful in the treatment of psychotic disorders.

8 Claims, No Drawings

DISUBSTITUTED MORPHOLINE, OXAZEPINE OR THIAZEPINE DERIVATIVES, THEIR PREPARATION AND THEIR USE AS DOPAMINE D4 RECEPTOR ANTAGONISTS

This application is a divisional of co-pending application Ser. No. 09/242,693, filed on Feb. 23, 1999. application Ser. No. 09/242,693 is the national phase of PCT International Application No. PCT/EP97/04587 filed on Aug. 22, 1997 under 35 U.S.C. §371. The entire contents of each of the above-identified applications are hereby incorporated by reference.

The present invention relates to novel pharmaceutically active disubstituted heterocyclic compounds with high affinity for central dopaminergic receptors. The compounds of the present invention are antagonists of the dopamine $D_4$ receptor and are useful in the treatment of central nervous system disorders, especially psychotic disorders such as schizophrenia.

BACKGROUND

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

The "dopamine hypothesis" of schizophrenia predicts an increased activity of dopamine neurotransmission in the brain. This hypothesis is supported by observations that drugs, such as amphetamine and cocaine, which indirectly stimulate the endogenous dopamine system by a dopamine release and reuptake inhibition are capable of eliciting a psychosis resembling acute paranoid schizophrenia. The fact that classical antipsychotic drugs produce their therapeutic effect by blocking central dopamine $D_2$ receptors also lends credence to the "dopamine hypothesis". It is however a serious drawback to the classical anti-psychotic drugs that the blockade of dopamine $D_2$ receptors also leads to extrapyrimidal side effects (EPS).

Clozapine is the only neuroleptic agent that improves the "positive" and "negative" symptoms of schizophrenia without producing EPS. The mechanism of action of Clozapine remains elusive, but has been proposed to be due, in part to a greater blockade of dopamine $D_4$ receptors compared to $D_2$ receptors, and also to a blockade of serotonin 5-HT2A receptors. It is considered that compounds which can interact selectively with the dopamine $D_4$ receptor subtype, whilst having a less pronounced action at the $D_2$ subtype will be less prone to give the side-effects associated with classical antipsychotic drugs while maintaining a beneficial level of antipsychotic activity.

The compounds of the present invention possess a high and selective affinity for dopamine $D_4$ receptors relative to the dopamine $D_2$ receptors.

As the compounds of the present invention are antagonists of the dopamine $D_4$ receptor they are predicted to be useful for the treatment of psychotic disorders such as schizophrenia.

Dopamine receptors are important for many functions in the animal body, For example, altered functions of these receptors participate in the genesis of psychosis, addiction, sleep, feeding, learning, memory, sexual behaviour, regulation of immunological responses and blood pressure. Since dopamine receptors control a great number of pharmacological events, compounds that act preferentially on the dopamine $D_4$ receptor may exert a wide range of therapeutic effects in humans. The compounds of the present invention may therefore also be useful for the treatment of conditions such as sleep disorders, sexual disorders, gastrointestinal disorders, various form of psychosis (affective psychosis, nonorganic psychosis), personality disorders, psychiatric mood disorders, conduct and impulse disorders, schizophrenic and schizoaffective disorders, conduct and impulse disorders, polydipsia, bipolar disorders, dysphoric mania, anxiety and related disorders, obesity, emesis, learning disorders, memory disorders, Parkinson's disease, depression, neuroteptic malignant syndrome, hypothalamic pituitary disorders, congestive heart failure, chemical dependencies such as drug and alcohol addictions, vascular and cardiovascular disorders, ocular disorders (including glaucoma), dystonia, tardive dyskinesia, Gilles De La Tourette's syndrome and other hyperkinesias, dementia, ischaemia, movement disorders such as akathesia, hypertension and diseases caused by a hyperactive immune system such as allergies and inflammation.

PRIOR ART

U.S. Pat. No. 4,088,814 describes certain morpholine derivatives having the formula

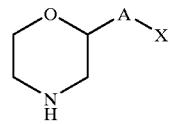

wherein A means ethylene or vinylene and X means optionally substituted phenyl. The compounds are claimed to have psychotropic activity, e.g. antidepressant and sedative activity. Some compounds also show analgesic activity. Compounds described herein having a benzyl group attached in position 4 are used as intermediates for the preparation of the therapeutically active compounds.

GB patent No. 1.138.405 describes certain morpholine derivatives having the formula

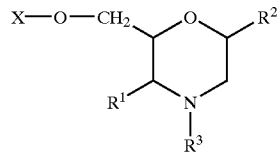

wherein $R^1$ and $R^2$ means hydrogen or alkyl, $R^3$ means hydrogen, alkyl, alkenyl, or cycloalkyl, and X means an optionally substituted aryl radical. The compounds described herein possess depressant action on the central nervous system, and are said to be useful in the treatment of anxiety, neurotic states and epilepsy. Some of the compounds are said to possess anti-depressant activity. The compounds described herein having a arylalkyl group attached in position 4 are used as intermediates for the preparation of the therapeutically active compounds.

A well known compound disclosed in the above patent is Viloxazine or 2-[(2-ethoxy-phenoxy)methyl]morpholine. This compound have no or only low affinity for the central dopaminergic $D_2$ and $D_4$ receptors.

GB patent No.1.310.236 describes certain morpholine derivatives which are useful as intermediates for the preparation of therapeutically active compounds.

OBJECTS OF THE INVENTION

It is an object of the present invention to provide novel disubstituted heterocyclic compounds and pharmaceutically-acceptable acid addition salts thereof which are useful for the treatment of central nervous system disorders, or diseases responsive to the blockade of dopamine $D_4$ receptors, especially psychotic disorders such as schizophrenia.

Another object of the present invention is to provide pharmaceutical compositions comprising the novel disubstituted heterocyclic compounds being useful for above purposes.

Still another object of the present invention is to provide a method of treating disorders or diseases responsive to the blockade of dopamine $D_4$ receptors using the novel disubstituted heterocyclic compounds.

Additional objects will be obvious from the following description, and others will be obvious to one skilled in the art.

SUMMARY OF THE INVENTION

The invention then, inter alia, comprises the following, alone or in combination:

A compound of the formula

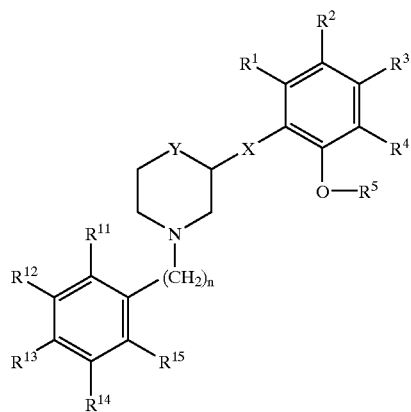

any of its enantiomers, or any mixture thereof, or a pharmaceutically acceptable acid addition salt thereof, wherein
$R^1$, $R^2$, $R^3$, $R^4$, $R^{11}$, $R^{12}$, $R^{13}$, $R^{14}$, and $R^{15}$ each independently are hydrogen, alkyl, alkoxy, halogen, trifluoromethyl, nitro, cyano, amino, acyl, aminocarbonyl, or acylamino;

$R^5$ is hydrogen, alkyl, alkoxyalkyl, or phenylalkyl;

X is —$CH_2$—Z—, —Z—$CH_2$—, —NH—CO—, —CO—NH—, or —CH=CH—; wherein Z is O, S, $CH_2$ or NH;

Y is O, —$CH_2$—W—, —W—$CH_2$—; wherein W is O, or S;

and n is 0, 1, or 2;

a compound as above which is (±)-N-(4-chlorobenzyl)-2-(2-methoxy-4-chloro-phenoxymethyl)-morpholine, or (±)-2-[(4-chloro-2-methoxyphenoxy)methyl]-4-(4-chlorobenzyl)perhydro oxazepine or a pharmaceutically acceptable acid addition salt thereof;

a pharmaceutical composition, comprising an effective amount of a compound as any above, or a pharmaceutically acceptable acid addition salt thereof, together with at least one pharmaceutically acceptable carrier or diluent:

the use of a compound having the formula

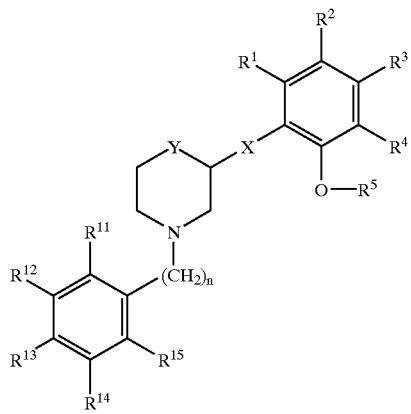

any of its enantiomers, or any mixture thereof, or a pharmaceutically acceptable acid addition salt thereof, wherein
$R^1$, $R^2$, $R^3$, $R^4$, $R^{11}$, $R^{12}$, $R^{13}$, $R^{14}$, and $R^{15}$ each independently are hydrogen, alkyl, alkoxy, halogen, trifluoromethyl, nitro, cyano, amino, acyl, aminocarbonyl, or acylamino;

$R^5$ is hydrogen, alkyl, alkoxyalkyl, or phenytalkyl;

X is —$CH_2$—Z—, —Z—$CH_2$—, —NH—CO—, —CO—NH—, or —CH=CH—; wherein Z is O, S, $CH_2$ or NH;

Y is O, —$CH_2$—W—, —W—$CH_2$—; wherein W is O, or S;

and n is 0, 1, or 2 for the manufacture of a medicament for the treatment of a disorder or disease of a living animal body, including a human, which disorder or disease is responsive to the blockade of dopamine $D_4$ receptors of the central nervous system;

the use of a compound as above for the manufacture of a medicament for the treatment of psychotic disorders including schizophrenia;

the use as above, wherein the compound employed is N-(4-chlorobenzyl)-2-(2-methoxy-4-chloro-phenoxymethyl)-morpholine, or (±)-2-[(4-chloro-2-methoxyphenoxy)methyl]-4-(4-chlorobenzyl)perhydro oxazepineor a pharmaceutically acceptable acid addition salt thereof;

a method for the treatment of a disorder or disease which is responsive to the blockade of dopamine $D_4$ receptors of the central nervous system comprising administering to a living animal body, including a human, in need thereof a therapeutically effective amount of a compound of the formula

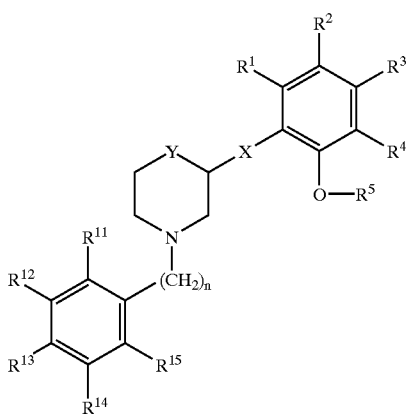

any of its enantiomers, or any mixture thereof, or a pharmaceutically acceptable acid addition salt thereof, wherein R¹, R², R³, R⁴, R¹¹, R¹², R¹³, R¹⁴, and R¹⁵ each independency are hydrogen, alkyl, alkoxy, halogen, trifluoromethyl, nitro, cyano, amino, acyl, aminocarbonyl, or acylamino;

R⁵ is hydrogen, alkyl, alkoxyalkyl, or phenylalkyl;

X is —CH₂—Z—, —Z—CH₂—, —NH—CO—, —CO—NH—, or —CH=CH—; wherein Z is O, S, CH₂ or NH;

Y is O, —CH₂—W—, —W—CH₂—; wherein W is O, or S;

and n is 0,1, or 2;

a method as above wherein the disorder or disease is a psychotic disorder, including schizophrenia; and a method for the preparation of a compound as above comprising the step of reacting a) reacting a compound having the formula

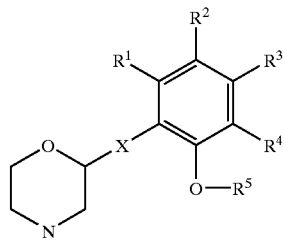

wherein R¹, R², R³, R⁴, R⁵, and X is as defined in claim 1, with a compound having the formula

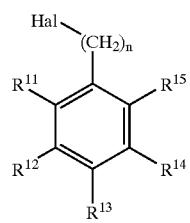

wherein R¹¹, R¹², R¹³, R¹⁴ and R¹⁵ is as defined in claim 1 and Hal is halogen, to form a compound of the invention; or b) reacting a compound having the formula

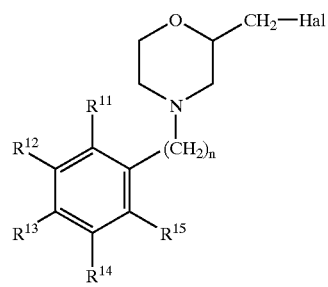

wherein R¹¹, R¹², R¹³, R¹⁴ and R¹⁵ is as defined in claim 1 and Hal is halogen, with a compound having the formula

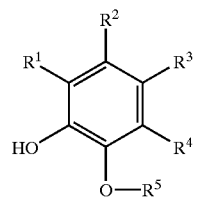

wherein R¹, R², R³, R⁴ and R⁵ is as defined in claim 1, to form a compound of the invention, whereafter a compound of the invention is optionally converted to another compound of the invention and/or to a pharmaceutically acceptable salt of a compound of the invention.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of preferably one to six carbon atoms or cyclic alkyl of preferably three to seven carbon atoms, including but not limited to, methyl, ethyl, propyl, isopropyl, butyl, isobutyl, t-butyl, pentyl, hexyl, cyclopropyl, cyclobutyl, cyciopentyl, cyclohexyl; methyl, ethyl, propyl and isopropyl are particularly preferred groups.

Acyl means —CO-alkyl wherein alkyl is as defined above.

Acylamino means Acyl-NH— wherein acyl is as defined above.

Amino is NH₂ or NH-alkyl or N-(alkyl)₂, wherein alkyl is as defined above.

The compounds of the invention are preferably oxazepines.

I.p. means intraperetoneally, which is a well known route of administration.

P.o. means peroral, which is a well known route of administration.

The compounds of the invention may be prepared in numerous ways. The compounds of the invention and their pharmaceutically acceptable derivatives may thus be prepared by any method known in the art for the preparation of compounds of analogous structure, and as shown in the representative example which follow.

Starting materials for the processes described in the present patent application are known or can be prepared by known processes from commercially available materials.

A compound of the invention can be converted to another compound of the invention using conventional methods.

The products of the reactions described herein are isolated by conventional means such as extraction, crystallizabon, distillation, chromatography, and the like.

Further, the compounds of this invention may exist in unsolvated as well as in solvated forms with pharmaceutically acceptable solvents such as water, ethanol the like. In general, the solvated forms are considered equivalent to the unsolvated forms for the purposes of this invention.

It will be appreciated by those skilled in the art that the compounds of the present invention contain chiral centres and that such compounds exist in the form of isomers (i.e. enantiomers). The invention includes all such isomers and any mixtures thereof including racemic mixtures.

A prefered embodiment of the invention comprises the compounds of claim 1 wherein Y is —O— or —CH$_2$—O— and X is —CH$_2$— with S configuration.

The pure enantiomers can be obtained by the use of optically active starting materials.

Racemic forms can also be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or I-(tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Biology

The compounds of the present invention exhibit a high affinity for dopamine $D_4$ receptors and a much lower affinity for dopamine $D_2$ receptors. The affinity of certain compounds of the invention for the dopamine $D_2$ receptor and the dopamine $D_4$ receptor have been determined by measuring the ability of the compounds to inhibit the binding of $^3$H-spiperone to these receptors using the procedure described below:

INTRODUCTION

Dopamine is involved in several important functions, excitatory and inhibitory, via dopaminergic receptors in the central nervous system (CNS) and in the periphery. Dopaminergic systems are of particular interest because of their role in the etiology and management of various CNS disorders, such as Parkinson's disease and schizophrenia.

Dopamine receptors were originally classified into two main groups: $D_1$ and $D_2$. The five currently cloned dopamine receptors fall into these classes. Thus, the $D_1$-like receptors include $D_1$ and $D_5$, while the $D_2$-like receptors include $D_2$, $D_3$ and $D_4$. Dopaminergic receptors are coupled via two distinct G-proteins to intracellular signalling mechanisms. $D_1$ and $D_2$-like receptors are coupled respectively to stimulation and inhibition of the effector enzyme adenylyl cyclase, which produces the second messenger cAMP.

The $D_2$-like receptors can be labelled by the antagonist $^3$H-spiperone. As the ligand has the same affinity for $D_2$, $D_3$, and $D_4$ receptors, selective binding to i.e. $D_4$ receptors is only possible using recombinant receptors.

TEST PROCEDURES

I) In vitro Inhibition of $^3$H-spiperone Binding to $D_2$ dopamine Receptors

Tissue preparation: Preparations are performed at 0–4° C. unless otherwise indicated. Corpus Striatum from male Wistar rats (150–200 g) is homogenized for 5–10 sec in 10 ml KH$_2$PO$_4$ (50 mM, pH 7.4) using an Ultra-Turrax homogenizer. The suspension is centrifuged at 27,000×g for 15 min. The supematant is discarded and the pellet is resuspended in 50 mM KH$_2$PO$_4$, pH 7.4 (2000 ml per g of original tissue) and used for binding assays.

Assay: Aliquots of 0.5 ml tissue are added to 25 $\mu$l of test solution and 25 $\mu$l of $^3$H-spiperone (0.2 nM, final concentration), mixed and incubated for 20 min at 37° C. Non-specific binding is determined using butadamol (1 $\mu$M, final concentration). After incubation the samples are placed on ice for 10 min. The assay is terminated by addition of 5 ml of ice-cold buffer and poured directly onto Whatman GF/C glass fibre filters (presoaked in 0.1% PEI for at least 20 min) under suction and immediately washed with 5 ml ice-cold buffer. The amount of radioactivity on the filters is determined by conventional liquid scintillation counting. Specific binding is total binding minus non-specific binding.

II) In Vitro Inhibition of $^3$H-spiperone Binding to $D_{4.2}$ Dopamine Receptors (Human Recombinant)

Tissue preparation: Frozen membranes from Chinese Hamster Ovary (CHO) cells transfected with the human recombinant $D_{4.2}$ dopamine receptor (RBI, D-195). Membranes are suspended in 10 mM Tris-HCl (pH 7.2) containing 2 mM EDTA, and stored tightly sealed at −80° C.

Asssay: The membranes are thawed and diluted in incubation buffer (50 mM Tns-HCl, pH 7.4, containing 120 mM NaCl, 5 mM KCl, 5 mM MgCl$_2$ and 1 mM EDTA) —0.25 ml of membranes to 4.75 ml of incubation buffer. Aliquots of 100 $\mu$l of diluted membranes are added to 100 $\mu$l of test solution and 50 $\mu$l of $^3$H-spiperone (0.5nM, final concentration). Finally, 750 $\mu$l incubation buffer is added and the assay mixture is incubated for 60 min at 25° C. Non-specific binding is determined using haloperidol (1 $\mu$M, final concentration). After incubation the assay is terminated by rapid filtration over GF/C glass fibre filters (presoaked in 0.1% PEI for at least 20 min), then washed twice with 5 ml ice cold 50 mM Tris-HCl in 0.9% NaCl at pH 7.4. The amount of radioactivity on the filters is determined by conventional liquid scintillation counting. Specific binding is total binding minus non-specific binding.

RESULTS

The test values are given as $IC_{50}$ (the concentration of the test substance which inhibits the specific binding of $^3$H-spiperone by 50%).

The results obtained by testing certain compounds of the invention are presented in table 1:

TABLE 1

| Compound | $D_4(\mu M)$ | $D_2(\mu M)$ |
|---|---|---|
| (±)-N-(4-chlorobenzyl)-2-(2-methoxy-4-chloro-phenoxymethyl)-morpholine | 0.004 | >10.00 |
| (±)-2-{(4-chloro-2-methoxyphenoxy)-methyl}-4-(4-chlorobenzyl)perhydro oxazepine | 0.0025 | >10.00 |

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dicnlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Methods of Treating

The compounds of this invention possess potent dopamine $D_4$ receptor blocking activity. This property make the compounds of the present invention extremely useful in the treatment of psychotic disorders such as schizophrenia as well as other disorders sensitive to the blockade of dopamine $D_4$ receptors. The compounds of this invention may accordingly be administered to a living animal body, including a human, in need of treatment, alleviation, or elimination of an indication associated with or responsive to the blockade of dopamine receptors, especially the dopamine $D_4$ receptor. This includes especially schizophrenia and other psychotic disorders. Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLES

General: All reactions involving air sensitive reagents or intermediates were performed under nitrogen.

Example 1

N-(4-Chlorobenzyl)-N-(2-hydroxyethyl)amine

Ethanolamine (56.9 g, 931 mmol) and sodium hydroxide (7.44 g, 186 mmol) were mixed in isopmpanol (50 ml) and 4-chlorobenzyl chloride (30 g, 186 mmol) was added at such a rate that a mild reflux was achieved. The mixture was then refluxed for another 30 min. Evaporation of the solvent was followed by the addition of methylene chloride (50 ml). The solids were filtered off and the solvent was evaporated from the filtrate. The residual oil was distilled under oil pump vacuum and the fraction at 125–126° C. (0.1 mm Hg) was collected. Yield 27 g, 78%.

N-(4-Chlorobenzyl)-N-(3-hydroxypropyl)amine

N-(4-Chlorobenzyl)-N-(3-hydroxypropyl)amine was prepared analogously starting with 3-hydroxypropylamine. bp 128–130° C. 0.1 mm Hg. Yield 29%.

Example 2

(±)-4-(4-Chlorobenzyl)-2-(chloromethyl)perhydro-1, 4-oxazepin (±)-4-(4-Chlorobenzyl)-2-(chloromethyl)perhydro-1,4-oxazepin was prepared analogously to the method for the preparation of (±)-4-benzyl-2-(chloro-methyl)-perhydro-1, 4-oxazepin described in K. Araki et al. *J. Med. Chem.* 36, 1356 (1993), using N-(4-Chlorobenzyl)-N-(3-hydroxypropyt)amine as starting material. Yield 29%.

Example 3

(±)-4-Benzyl-2-chloromethylmorpholine (±)-4-Benzyl-2-chloromethylmorpholine was prepared according to F. Loftus, *Synth. commun.* 10, 59 (1980).

(±)-4-(4-Chlorobenzyl)-2-chloromethylmorpholine

The title compound was prepared analogously using N-(4-chlorobenzyl)-N-(2-hydroxyethyl)amine and epichlorohydrn as the starting material. bp 106–120° C. at 0.3 mm Hg.

Example 4

R-4-(4-Chlorobenzyl)-2-chloromethylmorpholine and S-4-(4-Chlorobenzyl)-2-chloromethylmorpholine R-4-(4-Chlorobenzyl)-2-chloromethylmorpholine and S-4-(4-chlorobenzyl)-2-chloromethylmorpholine was prepared analogously to the preparation of R- and S-4-(4-fluorobenzyl)-2-chloromethylmorpholine as described in T. Morie, S. Kato, H. Harada, and J. Matsumoto *Heterocycles*, 38 (1994).

Example 5

(±)-4-Benzyl-2-[(2-ethoxyphenoxy)-methyl]morpholine (±)-4-Benzyl-2-[(2-ethoxyphenoxy)-methyl]morpholine was prepared according at example 18 (below). The product was obtained as an oil.

(±)-2-[(2-Ethoxyphenoxy)-methyl]morpholine hydrochloride

The title compound was prepared by hydrogenation of (±)-4-benzyl-2-[(2-ethoxyphenoxy)-methyt]morpholine over 5% Pd/C in ethanol: 1 M aqueous HCl 3:1.mp 176—179° C. Yield 96%.

Example 6

2-Bromo-4-chloroanisole

Anisole (10 g, 70.1 mmol) was dissolved in carbon tetrachloride (200 ml) and iron powder (6.0 g, 105 mmol Fe)was added. Bromine (4 ml, 77.1 mmol) was added at 0° C. The temperature was allowed rise to room temperature over one hour. Washing with aqueous sodium sulfite three times was followed by washing with aqueous sodium hydroxide (4 M). Drying over magnesium sulfate and evaporation gave the title compound. Yield 5.63 g, 36%.

Example 7

5-Chloro-2-methoxy Benzeneboronic Acid

A solution of 2-bromo-4-chloroanisole (5.0 g, 22.6 mmol) in dry THF (60 ml) under nitrogen was cooled to −70° C. and n-butyl lithium (12.4 ml of a 2.0 M solution in hexanes, 24.8 mmol) was added. After 10 min. at −70° C. trIbutyl borate (8.5 ml, 31.4 mmol) was added and the temperature was allowed to rise to room temperature overnight. Aqueous hydrochloric acid (40 ml, 2 M) was added and the product was extracted with 2×60 ml ether. The ethereal phase was extracted with aqueous sodium hydroxide (2×40 ml, 1 M). Acidification with concentrated HCl during ice-cooling gave a precipitate that was dissolved in ether. Drying over magnesium sulfate and evaporation of the solvent gave the title compound. Yield 1.93 g, 46%.

Example 8

5-Chloro-2-methoxyphenol

A solution of 5-chloro-2-methoxy benzeneboronic acid (1.9 g, 10 mmol) in hydrogen peroxide (2.04 ml, 30% solution) and ethanol 40 ml was refluxed for 30 min. Water was added and the product was extracted with two portions of ethyiacetate. Drying over magnesium sulfate and evaporation of the solvent gave the product as an oil. Yield 1.05 g, 65%.

Example 9

4-Iodo-2-methoxyphenol

4-Iodo-2-methoxyphenol was prepared according to the method described by K. J. Edgar and N. Falling, *J. Org. Chem.* 55, 5287 (1990). Guaiacol (50.0 g, 402 mmol), sodium iodide (60.5 g, 402 mmol) was dissolved in methanol (800 ml) and cooled to 0° C., and sodium hydroxide (16.0 g, 402 mmol) was added at such a rate that the temperature did not exceed 5° C. An aqueous solution of sodium hypochlorite (750 ml, 72% solution, 402 mmol) was added during 45 min. The temperature was not allowed to exceed 0° C. After completed addition it was stirred for another 10 minutes at 0° C. First aqueous hydrochloric acid (100 ml, 4 M solution) and then sodium sulifite (200 ml saturated aqueous solution) was added. The product was extracted with ether was followed by drying over magnesium sulfate. Evaporation of the solvent was followed by distillation and the fraction at 105–106° C. at 0.1 mm Hg was collected. Yield 55 g, 54%.

Example 10

2-Chloro-4-hydroxy-5-methoxybenzoic Acid

2-Chloro-4-hydroxy-5-methoxybenzoic acid was prepared according to L. C. Raiford and D. J. Potter *J. Am. Chem. Soc.* 55, 1682 (1933).

Example 11

4-Acetoxy-2-chloro-5-methoxybenzoic Acid

4-Acetoxy-2-chloro-5-methoxybenzoic acid was prepared by acetylation of 2-chloro-4-hydroxy-5-methoxybenzoic acid.

Example 12

5-Chloro-4-cyclopropylaminocarbonyl-2-methoxyphenol

A solution of 4-acetoxy-2-chloro-5-methoxybenzoic acid (8.6 g, 35.2 mmol) and triethylamine (8.9 g, 88 mmol) in dry dichloromethane (100 ml) was cooled to 0° C. and ethylchloroformate (7.6 g, 70 mmol) was added at such a rate that the temperature stayed below 5° C. After 1 h cyclopropylamine (6.0 g, 105 mmol) was added. After stirring overnight at room temperature the organic phase was washed with water (2×200 ml). Drying over magnesium sulfate was followed by reduction of the solvent volume to half. Petrol ether was added and the product was filtered off. Yield 570 mg, 6.7%, mp 214–216° C.

Example 13

2-(2-Methoxy-1-ethoxy)-phenol

Catechol (10.0 g, 91 mmol), bromoethylmethylether (12.6 g, 91 mmol), and potassium carbonate (12.6 g, 91 mmol) were mixed in ethanol (100 ml) and refluxed for 15 h. The solvent was evaporated and dichioromethane (200 ml) was added. The inorganics were filtered off and the solvent was removed in vacuum. Chromatography on silica gel with 0.5% methanol in dichloromethane as the eluent gave the title compound. Yield 4.5 g, 29%.

Example 14

2-Epoxy-1-(2-methoxyphenoxy)-propane

Guaiacol (8.6 g, 69 mmol), potassium t-butoxide (7.8 g, 69 mmol), epichlorohydrin (19.3 g, 209 mmol), and 18-crown-6 (0.8 g) were mixed in t-butanol (100 ml) and heated to 50° C. for 2 h. Water was added and the product was extracted with two portions of dichlorometane. Washing with water, twice, was followed by drying and evaporation. Quantitative yield.

Example 15

2-[(2-Methoxyphenoxy)methyl]-morpholine

A mixture of 2-epoxy-1-(2-methoxyphenoxy)-propane (13.0 g, 72 mmol), 2-aminoethylhydrogensulfate (51 g, 361 mmol), potassium hydroxide (41 g, 722 mmol) in isopropanol (300 ml) and water 100 ml was refluxed for 8 h. Water was added and the product was extracted with two portions of ethylacetate. Drying and evaporation gave a crude product that was used without further purification. Yield 9.2 g.

Example 16

2-[(5-Chlorobenzoxazolin-2-one-1-yl)-methyl]-4-(4-chlorobenzyl)-morpholine

2-[(5-Chlorobenzoxazolin-2-one-1-yl)-methyl]-4-(4-chlorobenzyl)-morpholine was prepared from 5-chlorozoxazone and (±)-4-(4-chlorobenzyl)-2-chloromethyl-morpholine according to example 18. mp 160–164° C. (As the oxalate). The free base was used in further reactions.

Example 17

(±)-2-[(2-methoxyphenoxy)methyl]-4-(4-trifluoromethylbenzyl)morpholine Oxalic Acid Salt The crude 2-[(2-methoxyphenoxy)methyl]morpholine (2.0 g, 9.0 mmol) was mixed with 4-trifluoromethylbenzytbromide (2.58 g 10.8 mmol), potassium carbonate (6.84 g, 49.5 mmol) in ethanol (50 ml) and refluxed for 3.5 h. Water was added and the product was extracted with 2 portions of ethyl acetate. Drying and evaporation gave the crude free base. Dissolution in ether and precipitation with oxalic acid gave a salt that was purified by recrystallization from ethanol and then THF. Yield 430 mg, 10%, mp 101–108° C.

The following compounds were prepared analogously:
(±)-4-Benzyl-2-[(2-methoxyphenoxy)-methyl]morpholine oxalic acid salt. mp 124–133° C.
(±)-4-(3-Chlorobenzyl)-2-[(2-methoxyphenoxy)methyl] morpholine oxalic acid salt. mp 132–136° C. (±)-4-(4-Chlorobenzyl)-2-[(2-methoxyphenoxy)methyl] morpholine oxalic acid salt. mp 139–142° C.
(±)-4-Benzyl-2-[(5-chloro-2-methoxyphenoxy)methyl] morpholine oxalic acid salt. mp 166–168° C.
(±)-4-Benzyl-2-[(4-iodo-2-methoxyphenoxy)methyl] morpholine oxalic acid salt. mp 160–163° C.
(±)-4-(3,4-Dichlorobenzyl)-2-[(2-methoxyphenoxy)methyl] morpholine oxalic acid salt. mp 140–143° C.
(±)-4-(4-Chlorobenzyl)-2-[(2-ethoxy-4-iodophenoxy) methyl]morpholine. mp 86–90° C.

Example 18

(±)-4-(4-Chlorobenzyl)-2-[(4-chloro-2-methoxyphenoxy) methyl]morpholine oxalic acid salt. A mixture of (±)-4-(4-chlorobenzyl)-2-chloromethyimorphoiine (10.0 g 38.5 mmol), 4-chloro-2-methoxyphenol (9.0 g, 58 mmol), potassium ethoxide (6.5 g, 77 mmol), and 18-crown-6 (10.2 g, 38.5) was refluxed in toluene (100 ml) for 34 h. Water (200 ml) was added and the phases were separated. Drying and evaporation of the toluene phase was followed by column chromatography on silica gel with 3% ethanol in dichloromethane as eluent. The free base was dissolved in ether and precipitated with oxalic acid to give the title compound. Yield 10.3 g, 57%, mp 133–139° C.

The following compounds were prepared analogously:
(±)-4-(4-Chlorobenzyl)-2-[(5-nitro-2-methoxyphenoxy) methyl]morpholine oxalic acid salt. mp 176–177° C.
(±)-4-(4-Chlorobenzyl)-2-[(2-ethoxyphenoxy)methyl] morpholine oxalic acid salt. mp 122–127° C.
(±)-4-Benzyl-2-[(2-benzyloxyphenoxy)methyl]morpholine oxalic acid salt. mp 79–84° C.
(±)-4-(4-Chlorobenzyl)-2-[(5-chloro-4-cyclopropylaminocarbonyl-2-methoxy-phenoxy)methyl] morpholine. mp 159–162° C.
(±)-4-(4-Chlorobenzyl)-2-[(2-methoxyethoxyphenoxy) methyl]morpholine oxalic acid salt. mp 122–127° C.
(±)-4-(4-Chlorobenzyl)-2-[(2-ethoxyphenoxy)methyl] perhydro oxazepine. Oil.
(±)-4-(4-Chlorobenzyl)-2-[(5-chloro-2-methoxyphenylamino)-methyl]morpholine oxalic acid salt was prepared using 5-chloro-2-methoxyaniline instead of a phenol. A reaction temperature of 40° C. was used in this case. mp 169–171° C.
(±)-2-[(2,6-Dimethoxyphenoxy)methyl]-4-(4-chlorobenzyl) morpholine oxalic acid salt. mp 105–107° C.
(±)-4-(4-Chlorobenzyl)-2-[(2-isopropoxyphenoxy)methyl] morpholine oxalic acid salt. mp 89–90° C.
(±)-2-[(2,3-Dimethoxyphenoxy)methyl]-4-(4-chlorobenzyl) morpholine oxalic acid salt. mp 139–141° C.
(±)-4-(4-Chlorobenzyl)-2-[(4-chloro-2-ethoxyphenoxy) methyl]morpholine. The product was isolated as the free base. mp 88–90° C.
(±)-4-(4-Chlorobenzyl)2-[(2-methoxyphenylthio)methyl] morpholine oxalic acid salt. mp 101–103° C.
(±)-4-(4-Chlorobenzyl)-2-[(4-chloro-2-ethoxyphenoxy) methyl]perhydro oxazepine oxalic acid salt. mp 77–81° C.
(±)-4-(4-Chlorobenzyl)-2-[(5-chloro-2-ethoxyphenoxy) methyl]morpholine. mp 85–87° C.
(±)-2-[(2-Acety-4-chlaraphenoxy)methyl]-4-(4-chlorobenzyl)perhydro oxazepine oxalic acid salt. mp 148–151° C.
(±)-2-[(4-chloro-2-methoxyphenoxy)methyl]-4-(4-chlorobenzyl)perhydro oxazepine oxalic acid salt. mp 127–129° C.
(R)-4-(4-Chlorobenzyl)-2-[(4-chloro-2-methoxyphenoxy) methyl]morpholine oxalic acid salt. Was prepared using R-4-(4-chlorobenzyl)-2-chloromethyimorpholine as starting material. mp 150–151° C.
(S)-4-(4-Chlorobenzyl)-2-[(4-chloro-2-methoxyphenoxy) methyl]morpholine oxalic acid salt. Was prepared using S-4-(4-chlorobenzyl)-2-chloromethylmorpholine as starting material.
(±)-2-[(2-methoxy-5-nitrophenoxy)methyl]-4-(4-chlorobenzyl)perhydro oxazepine oxalic acid salt. mp 140–143° C.

Example 19

(±)-1-[(4chlorobenzyl)morpholins-2-yl]-2-(2-methoxyphenyl)ethene Oxalic Acid Salt A mixture of N-(4-chlorobenz)-N-(2-hydroxyethyl) amine (2.00 g, 10.8 mmol) and cis-1,4-diacetoxy-2-buten (2.78 g, 16.2 mmol), trethylamine (3.26 g, 32.3 mmol), tetrakis trphenylphosphino palladium(0) (0.31 g, 0.27 mmol) in THF (20 ml) was refluxed ovemight. DMF (10 ml)

was added and the THF was stripped off in vacuum. Addition of 2-iodoanisole (3.8 g, 16.2 mmol) and diisopropylethylamine (2.8 g, 21.6 mmol) was followed by heating to 130° C. overnight. Ether was added and the organics were washed twice with aqueous sodium hydroxide (1 M). Chromatography on silica gel with dichloromethane with 1% methanol as the eiuent gave the free base. Dissolution in ether and precipitation with oxalic acid gave the title compound. Yield 1.0 g, 21%. mp 178–180° C.

(±)-4-(4-Chlorobenzyl)-2-[2-(2-methoxyphenoxy)eth-1-yl]morpholine oxalic acid salt. Was prepared by the hydrogenation of (±)-1-[(4-clorobenzyl)morpholin-2-yl]-2-(2-methoxyphenyl)ethene. mp 167–169° C.

Example 20

(±)-2-[(4-Acetyl-2-methoxyphenoxy)methyl]-4-benzylmorpholine oxalic acid salt. (±)-4-Benzyl-2-[(4-iodo-2-methoxyphenoxy)methyl]morpholine (360 mg, 0.82 mmol), 1-methoxyvin-1-yl trimethyltin (528 mg, 2.4 mmol), and palladium bis(triphenylphosphine)palladium(II)chloride (36 mg, 0.052 mmol) were refluxed in THF (15 ml) for 24 h. Water was added and was followed by extraction twice with ethyl acetate. The solvent was evaporated and the residue was stirred in aqueous hydrochloric acid (25 ml, 1 M) and methanol (10 ml) at 50° C. for 1 h. The product was extracted with ethyl acetate. Drying and evaporation of the solvent was followed by chromatography. The product was dissolved in ether and precipitated as the oxalate. Yield 40 mg. mp 122–127° C.

Example 21

(±)-2-[(5-Amino-2-methoxyphenoxy)methyl]-4-(4-chlorobenzyl)-morpholine oxalic acid salt. Prepared by the catalytic hydrogenation of (±)-4-(4-chlorobenzyl)-2-[(5-nitro-2-methoxyphenoxy)methyl]morpholine. mp 80–110° C.

Example 22

(±)-4-(4-Chlorobenzyl)-2-[(4-chloro-2-hydroxyphenylamino)methyl]morpholine oxalic acid salt. To solution of 2-[(5-chlorobenzoxazolin-2-one-1-yl)methyl]-4-(4-chlorobenzyl)morpholine (1.5 g, 3.8 mmol) in dimethoxyethane (8 ml) was added aqueous sodium hydroxide (3.8 ml of a 4 M solution, 15.3 mmol). After being stirred at 50° C. for 1 h water was added and the solids were filtered off. The filtrate was extracted twice with ethyl acetate. Drying and evaporation gave the free base. The product was then precipitated by dissolution in ether and addition of a saturated ethereal solution of oxalic acid. Yield 1.05 g, 61%. mp 177–179° C.

Example 23

(±)-4-(4-nitrobenzyl-2-[2-ethoxyphenoxy)methyl]morpholine oxalic acid salt. A mixture of (±)-2-[(2-ethoxyphenoxy)methyl]morpholine hydrochloride (3.0 g, 11.0 mmol) and 4-nitrobenzylbromide (2.37 g, 11.0 mmol) and potassium carbonate (1.52 g, 11.0 mmol) in DMF (30 ml) was heated to 80° C. for 4 h. Aqueous sodium hydroxide (50 ml) was added and the product was extracted twice with ether. Drying and evaporation gave the crude product. Chromatography on silica gel with dichlorometane +3% ethanol as the eluent. The product was dissolved in ether and precipitated as the oxalate. Yield 72% mp 113–114° C.

Example 24

(±)-4-(4-Chlorobenzyl)-2-[(4-cyano-2-ethoxyphenoxy)methyl]morpholine oxalic acid salt. A mixture of (±)-4-(4-chlorobenzyl)-2-[(2-ethoxy-iodaphenoxy)methyl]morphomine (1.0 g, 2.1 mmol), zinc cyanide (0.17 g, 1.4 mmol) and tetrakis(triphenylphosphino)palladium(0) (349 mg, 0.3 mmol) in DMF (15 ml) was heated to 80° C. for 3 h. Water was added and the solids were filtered off. The filtrate was extracted twice with ethyl acetate. Drying over magnesium sulfate was followed by evaporation. The crude product was dissolved in ether and an ethereal solution of oxalic acid was added to precipitate the product mp 133–138° C.

What is claimed is:

1. A compound of formula (I)

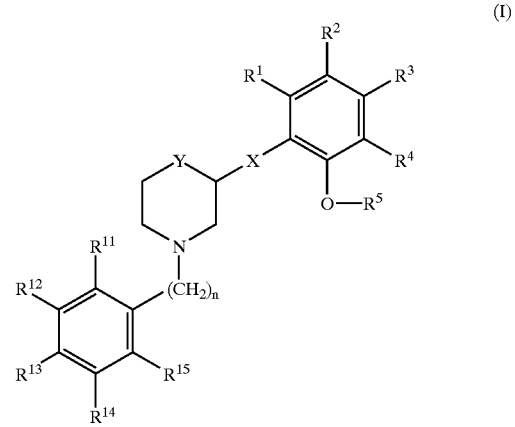

any of its enantiomers or any mixture thereof, or a pharmaceutically acceptable acid addition salt thereof, wherein:

$R^1$, $R^2$, $R^3$, $R^4$, $R^{11}$, $R^{12}$, $R^{13}$, $R^{14}$, and $R^{15}$ each independently are hydrogen, alkyl, alkoxy, halogen, trifluoromethyl, nitro, cyano, amino, aminoalkyl, aminodialkyl, acyl, aminocarbonyl, or acylamino, provided that $R^{11}$, $R^{12}$, $R^{13}$, $R^{14}$, and $R^{15}$ are not all hydrogen at the same time;

$R^5$ is hydrogen, alkyl, alkoxyalkyl, or phenylalkyl;

X is —CH$_2$—Z—, —Z—CH$_2$—, —NH—CO—, —CO—NH— or —CH=CH—, wherein Z is O, S, CH$_2$, or NH;

Y is O; and n is 0, 1 or 2.

2. The compound of claim 1, wherein X is —CH$_2$—O— with S configuration.

3. The compound (±)-N-(4-chlorobenzyl)-2-(2-methoxy-4-chloro-phenoxymethyl)-morpholine or a pharmaceutically acceptable acid addition salt thereof.

4. A pharmaceutical composition comprising a therapeutically effective amount of at least one compound of claim 1, and at least one pharmaceutically acceptable carrier or diluent.

5. A method for the treatment of a disorder or disease which is responsive to the blockade of dopamine $D_4$ receptors of the central nervous system, wherein said disorder or disease is selected from the group consisting of sleep disorders, sexual disorders, gastrointestinal disorders, psychosis, personality disorders, psychiatric mood disorders, conduct disorders, impulse disorders, schizophrenic disorders, schizoaffective disorders, bipolar disorders, anxiety disorders, learning disorders, memory disorders, hypothalamic pituitary disorders, vascular disorders, cardiovascular disorders, ocular disorders, movement disorders, and diseases caused by hyperactive immune systems, comprising administering to a living animal body in need thereof a therapeutically effective amount of at least one compound of claim 1.

6. The method of claim 5, wherein the disorder or disease is schizophrenia.

7. A method for the preparation of a compound of claim 1 comprising the step of a) reacting a compound of formula (II)

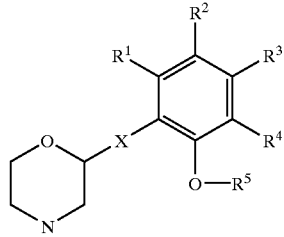

(II)

$R^1$, $R^2$, $R^3$, $R^4$, $R^5$, and X are as defined in claim 1, with of formula (III)

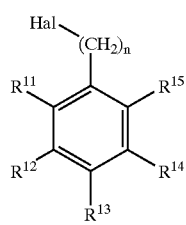

(III)

wherein $R^{11}$, $R^{12}$, $R^{13}$, $R^{14}$, and $R^{15}$ are as defined in claim 1 and Hal is halogen, to form a compound of formula (I); or b) reacting a compound of formula (IV)

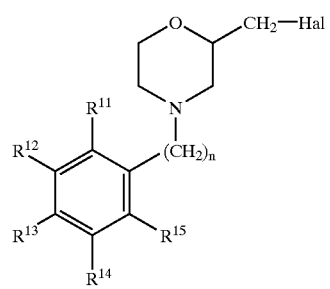

(IV)

wherein $R^{11}$, $R^{12}$, $R^{13}$, $R^{14}$, and $R^{15}$ are as defined in claim 1 and Hal is halogen, with a compound of formula (V)

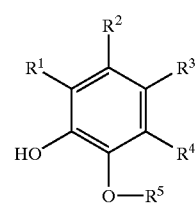

(V)

wherein $R^1$, $R^2$, $R^3$, $R^4$, and $R^5$ are as defined in claim 1, to form a compound of formula (I), whereafter the compound of formula (I) is optionally converted to another compound of formula (I) and/or to a pharmaceutically acceptable salt thereof.

8. A method for the treatment of schizophrenia, polydipsia, dysphoric mania, anxiety, obesity, emesis, Parkinson's disease, depression, neuroleptic malignant syndrome, congestive heart failure, chemical dependence on drugs, chemical dependence on alcohol, glaucoma, dystonia, tardive dyskinesia, Gilles De La Tourette's syndrome, dementia, ischaemia, akathesia, hypertension, allergies, and inflammation comprising administering to a living animal body in need thereof a therapeutically effective amount of at least one compound of claim 1.

\* \* \* \* \*